United States Patent

Cookston et al.

[11] Patent Number: 5,824,031
[45] Date of Patent: Oct. 20, 1998

[54] APPARATUS AND METHOD FOR DEFLECTING A TIP OF A LEAD OR CATHETER

[75] Inventors: H. Stephen Cookston, Malibu; Eli S. Gang, Los Angeles, both of Calif.

[73] Assignee: Cardio Source, Malibu, Calif.

[21] Appl. No.: 608,557

[22] Filed: Feb. 28, 1996

[51] Int. Cl.⁶ .......................... A61M 25/01; A61M 25/00; A61N 1/05
[52] U.S. Cl. ........................... 607/122; 128/772
[58] Field of Search ................ 607/122; 128/772

[56] References Cited

U.S. PATENT DOCUMENTS

| | | | |
|---|---|---|---|
| 4,676,249 | 6/1987 | Arenas et al. | 128/772 |
| 4,685,473 | 8/1987 | Karcher et al. | 128/772 |
| 4,944,727 | 7/1990 | McCoy | 128/772 |
| 5,025,799 | 6/1991 | Wilson | 128/772 |
| 5,037,391 | 8/1991 | Hammerslag et al. | 128/772 |
| 5,322,064 | 6/1994 | Lundquist | 607/122 |
| 5,327,905 | 7/1994 | Avitall | 607/122 |
| 5,328,467 | 7/1994 | Edwards et al. | 607/122 |
| 5,360,441 | 11/1994 | Otten | 607/122 |
| 5,478,330 | 12/1995 | Imran et al. | 607/122 |
| 5,487,757 | 1/1996 | Truckai et al. | 607/122 |
| 5,500,012 | 3/1996 | Brucker et al. | 607/122 |

*Primary Examiner*—William E. Kamm
*Assistant Examiner*—Carl H. Layno
*Attorney, Agent, or Firm*—Daniel L. Dawes

[57] ABSTRACT

A steerable or deflectable distal tip of a cardiac instrument is provided by creating a differential tension in a distal portion, causing the distal portion either to curve if originally straight, or to straighten if originally curved. The differential tension can be created by a pull or push wire disposed in a longitudinal lumen of the instrument, which wire is attached at its distal end to the instrument. In another embodiment, the differential tension is created by thermo-electrically heated by metallic strip which is disposed within a lumen within the instrument in the form of a stylet. In another embodiment, the stylet is deformed by virtue of differential tension being applied between a pair of strips comprising the stylet.

8 Claims, 4 Drawing Sheets

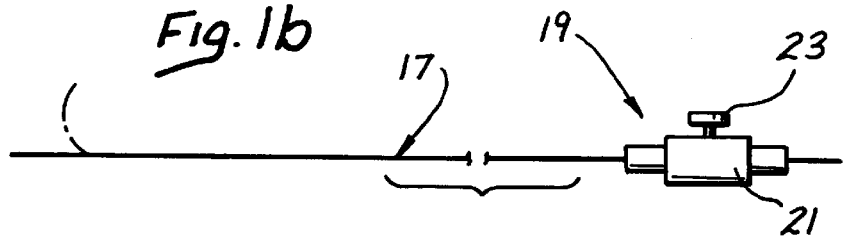
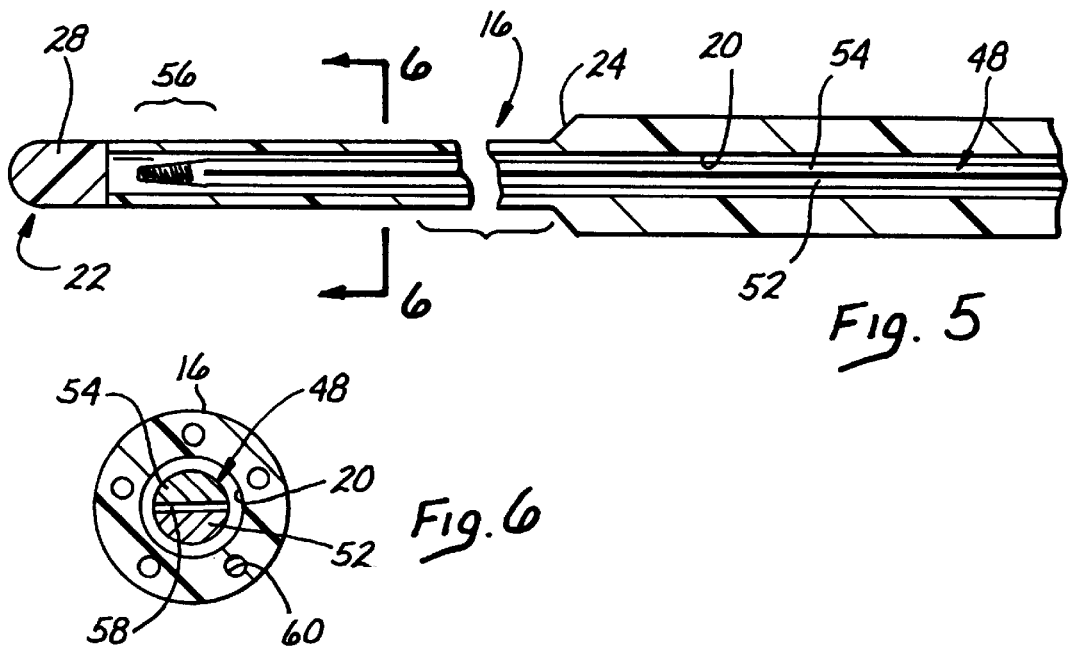
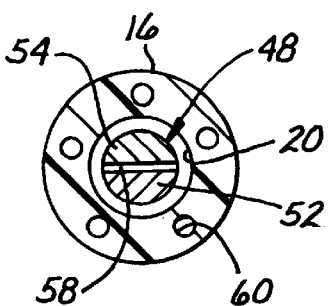
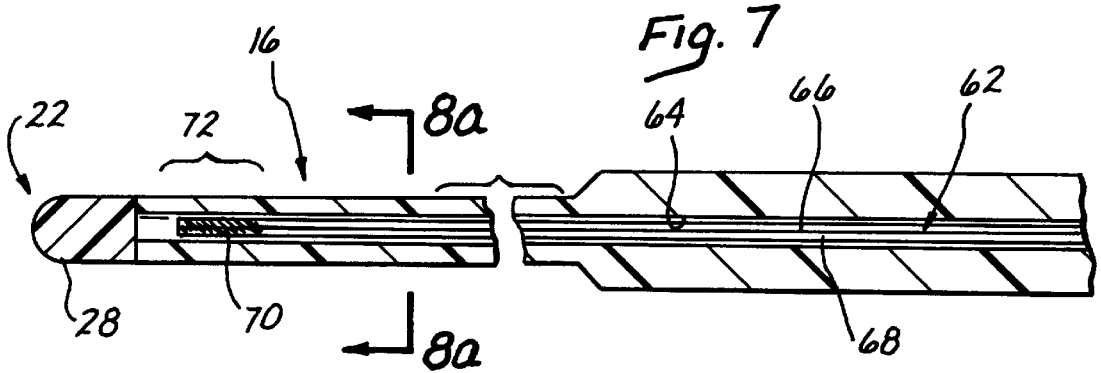
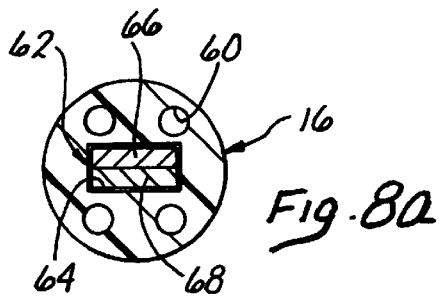
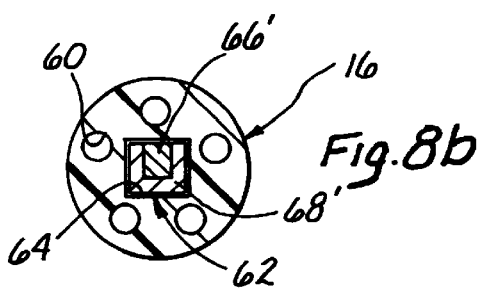

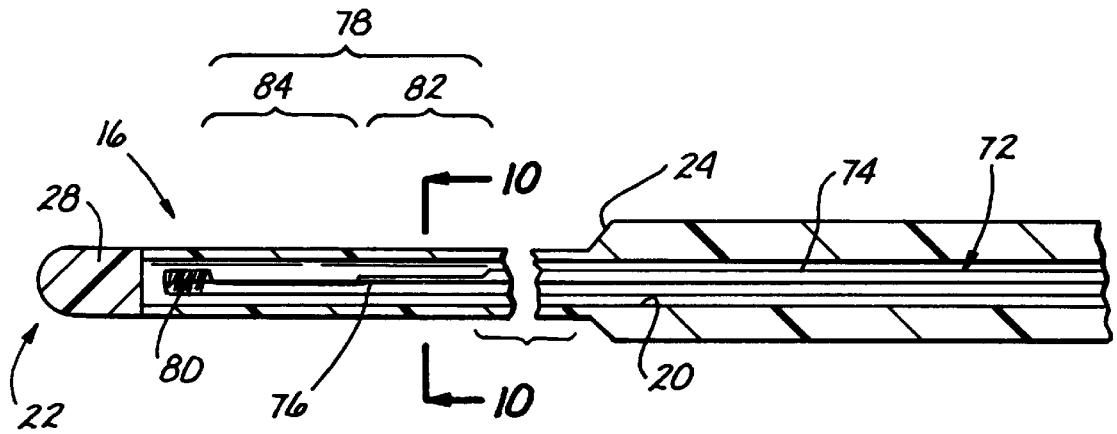
Fig. 9
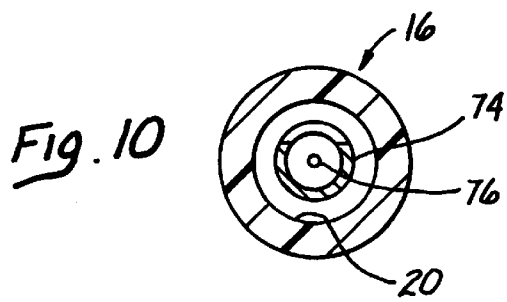
Fig. 10
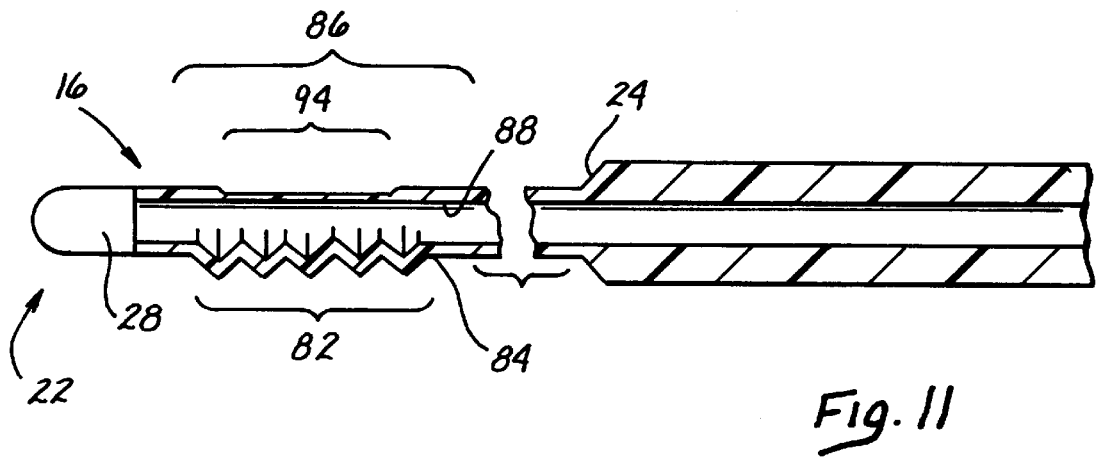
Fig. 11
Fig. 12
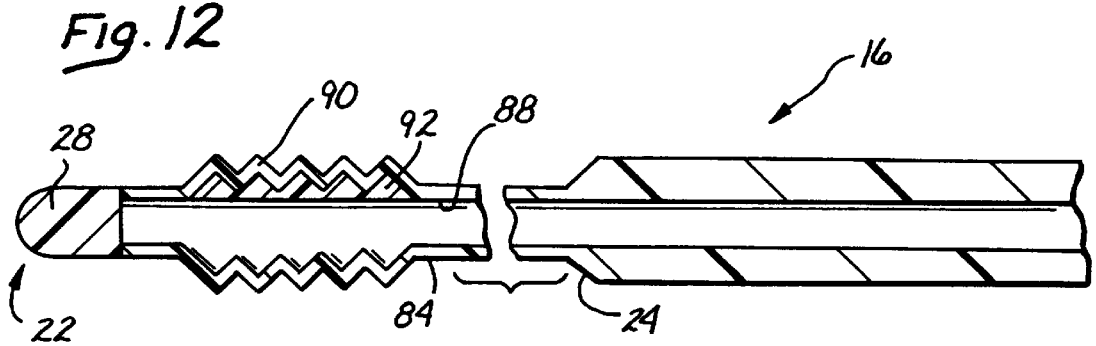

APPARATUS AND METHOD FOR DEFLECTING A TIP OF A LEAD OR CATHETER

BACKGROUND OF THE INVENTION

1. Field of the Invention

The invention relates to the field of cardiac leads and catheters, including pacemaker leads, defibrillator leads, ablation leads, mapping leads and the like, and in particular, to an apparatus and method for variably and controllably changing the curvature of the tip of such a cardiac lead.

2. Description of the Prior Art

Currently, during the implantation of a permanent cardiac pacemaker system, the leads are introduced into a vein either via a cut down or percutaneous sheath introduction and are positioned under fluoroscopy into either the right atrium, right ventricle, or both in the case of a dual chamber pacing system. The positioning of the pacemaker leads is the most time consuming and difficult aspect of the implantation. The current practice for lead placement requires the surgeon or cardiologist to advance the cardiac lead toward the heart through the veins until initial access is obtained. As the lead passes through the tributary veins into the subclavian vein and then into the right atrium of the heart, a straight stylet or wire must be disposed within a longitudinal lumen within the cardiac lead in order to give the lead sufficient strength and rigidity to proceed into the right atrium. An important aspect of proper placement is crossing of the tricuspid valve. In order to achieve this, the straight stylet is withdrawn and the physician fashions a curve at the tip of another stylet. Thereafter, most physicians continue advancing the lead with the curved tip stylet in place into the pulmonary artery outflow track to confirm right ventricle access and to rule out the possibility of entrance into the coronary sinus or coronary vein, which can mimic the appearance of a right ventricle placement under fluoroscopy. Once the physician has confirmed that placement of the lead is in fact in the pulmonary outflow track, the conventional practice requires the physician to then remove the curved stylet and partially readvance the original or another straight stylet into the lead. The cardiac lead is then carefully pulled back under direct fluoroscopic observation until the lead drops from the proximal portion of the pulmonary artery to the floor of the right ventricle, after which the physician advances the stylet to its fully advanced position within the lead to advance the lead to the distal most position of the right ventricular apex.

In the case of atrial lead placement, the lead is then positioned into either the right atrial appendage or is fixed by means of an active fixation screw or tines into or near the septum or other portion of the atrium selected by the physician. In the case where a ventricular lead is being implanted, the lead must be passed from the right atrium into the right ventricle through the tricuspid valve. Due the anatomy of the right ventricle, it is necessary to remove the straight stylet and then introduce a curved tip stylet, which the physician fashions manually from a standard straight stylet, so that the lead will have an appropriate shape, turn appropriately and pass through the tricuspid valve.

In the case where the lead does not have a screw fixation and is passive or has tines on the lead tip, the lead is then left in a visually appropriate position as determined by fluoroscopy and electrical testing is performed to confirm proper electrical contact. In the case of an active fixation lead, namely one having a screw-in-type tip, the attachment mechanism is then activated to secure the distal tip of the pacing lead into the endocardium at the selected position.

In a typical pacemaker implantation therefor, there are multiple exchanges of straight stylets and curved stylets which have been bent according to the physician's choice. The stylet is a thin solid wire, typically of about 0.014–0.018 inch in diameter. During handing, they can easily become bent or kinked, and thereafter cause great difficulty when an attempt is made to reinsert them through the narrow inner diameter of the lead's lumen, which may only be 0.019 inch in the case of a stylet of 0.018 inch diameter, typically providing no more than 0.0005 inch clearance on each side.

In addition, because the surgeon is working through an open wound, even the most fastidious surgeon will have blood on his gloves which will be transferred to the stylet. The blood congeals, and because of the small clearance, even a few drops of blood is sufficient to causing jamming of the stylet inside the lead body. When the stylet jams in the lead body, kinking of the stylet within the lead can occur, which kinks, in turn, will create new jams or problems with the insertion and retraction of the stylet from the lead.

The overall result of such difficulties is that operative time is greatly increased which results in much higher X-ray exposures to the patient, who is under continues fluoroscopy, including scattered X-ray exposure to the operating room staff, increased cost due to procedural time delays, and in some cases, the jamming is so severe that the cardiac lead must be removed from the heart for fear of insulation puncture, discarded and a new lead implanted, thereby at least doubling the lead cost used in the procedure as well as operative time.

Therefore, what is needed is some type of apparatus or method that eliminates the need for any stylet removal or hand fashioning of a curve in a stylet by the physician, and which therefore will dramatically shorten X-ray risks to the patient and to the staff. The method should dramatically reduce the total time of operation for a pacemaker implantation, thereby broadly reducing the cost of this procedure under national and private health care cost schedules.

The same methodology is used in placing transvenous defibrillating leads which, in essence, are large pacing leads positioned at the apex of the right ventricle.

The apparatus and method should be such that it is usable in both pediatric and adult patients with considerably different sized heart structures.

The apparatus and methodology should be applicable to any type of cardiac implantation used, including the atrial and ventricular placements with both passive and active fixation and any type of device that utilizes a lead or catheter.

BRIEF SUMMARY OF THE INVENTION

The invention is an improvement in a lead or catheter having a proximal and distal end and a longitudinal lumen defined at least part way therein. In the illustrated embodiment a cardiac lead or catheter is described, but the invention is not limited to cardiac applications. Generally, the term "lead" is used to refer to an elongated flexible instrument which in its normal intended use is coupled in some operative manner to a device which is interior to or implanted into the body, since the lead is intended to remain in place after implantation and first immediate use. The term "catheter" is generally used to refer to an elongated flexible instrument which in its normal intended use is coupled in some operative manner to a device which is exterior to the body, since the catheter is intended to be removed after implantation and after its first immediate use. The terms, however, are often used interchangeably in practice. For the purpose of this specification wherever one term "lead" or "catheter" is used it shall be deemed to include both meanings and may be referred to generically simply as "an elongated instrument" or "instrument".

The improvement comprises a deflector disposed in the lumen within at least the distal portion of the lead or catheter, or elongated instrument. The deflector is used by the surgeon to selectively impose a curvature on the distal portion of the instrument according to his own determination. As a result, variable curvatures can be selectively defined within the distal portion of the instrument. The term "deflector" is defined for the purposes of this specification to include both a means which is integrally and permanently built into the instrument, like a pull wire, and a means which is temporarily disposed into the instrument and then removed, like a stylet.

The deflector may impose a user-defined curvature on the distal portion of the instrument, which distal portion is otherwise without defined curvature, the deflector may impose a defined curvature on the distal portion of the instrument, where otherwise the distal portion is substantially straight, or the deflector may straighten the distal portion of the instrument which is otherwise provided with a prebiased curvature.

In one embodiment the deflector comprises a pull wire disposed within the lumen, attached at its distal end to the distal portion of the instrument. A proximal end of the pull wire extends to the proximal portion of the instrument and is retractable at least to a degree from the lumen to cause the distal portion to curve by user-selected amounts.

In another embodiment the deflector is a stylet disposable within the lumen and wherein deflection of the stylet is user-selected and varied. One version of the stylet comprises at least in part a thermoelectrically deformable strip. Ohmic heating of the strip causes the strip to curve and hence the distal portion of the instrument therewith. The thermoelectrically deformable portion of the stylet is disposed within the distal portion of the instrument. In another version of the stylet, it is comprised at least in part of a pair of differentially slidable wires connected at one end and disposed within the distal portion of the instrument. Differential tension of the wires with respect to each other causes the pair of wires to curve and hence the distal portion of the instrument therewith.

The illustrated embodiment shows the invention being used in a pacemaker lead. Other applications expressly contemplate use of the invention in a defibrillation lead, ablation lead, a sensing lead, pulmonary artery catheters, central venous catheters, diagnostic coronary catheters, intra-aortic balloon pump catheters, and PTCA/angioplasty catheters.

The invention is also defined as an improvement in a method for variably controlling the shape of cardiac instrument while being implanted comprising the step of curving a deflector disposed within a longitudinal lumen within the cardiac instrument at least along a distal portion of the instrument, and conformably curving the distal portion of the instrument in response to the curvature of the deflector. The deflector is curved according to user selection. Again the step of curving the deflector comprises establishing a differential tension between a first and second longitudinal element in at least the distal portion of the instrument. the degree of the differential tension determining the degree of curvature of the distal portion.

In one embodiment the step of establishing the differential tension comprises withdrawing a pull wire disposed in the longitudinal lumen defined in the instrument wherein the pull wire is fixed at its distal end to the distal portion of the instrument. In this case the first longitudinal element comprises the instrument and the second longitudinal element comprises the pull wire.

In another embodiment the step of establishing the differential tension comprises thermoelectrically heating two parallel elements of differential thermal expansion. In this case the first longitudinal element comprises one of the two parallel elements of differential thermal expansion, and the second longitudinal element comprises the other one of the two parallel elements of differential thermal expansion.

In still another embodiment the step of establishing the differential tension comprises longitudinally tensioning a first longitudinal portion of a stylet relative to a second longitudinal portion of the stylet. The longitudinal portions are disposed within the lumen within the distal portion of the instrument. In this case the first longitudinal element comprises the first longitudinal portion of the stylet. and the second longitudinal element comprises the second longitudinal portion of the stylet.

In another implementation the step of establishing the differential tension comprises differentially expanding or compressing one side portion of the instrument with respect to an opposing side portion of the instrument by manipulation of the deflector.

Therefore, without being limited to the use of a stylet the invention is defined as an improvement in a method for variably controlling the shape of cardiac instrument while it is being positioned comprising the step of curving at least a distal portion of the instrument by differentially expanding or compressing one side portion of the instrument with respect to an opposing side portion of the instrument by manipulation of a telescoping portion of the one side portion of the instrument. For example, the step of curving at least a distal portion of the instrument by differentially expanding or compressing one side portion of the instrument with respect to an opposing side portion of the instrument comprises inflating or evacuating respectively a folding lumen defined in the one side portion of the instrument. Alternatively, the placement of tensile filaments in the instrument can be used to stretch or compress telescopic portions of the distal tip of the instrument in combination or not with pressurization or evacuation of telescopic lumens defined in the instrument.

The invention can be better visualized by now turning to the following drawings, wherein like elements are referenced by like numerals.

BRIEF DESCRIPTION OF THE DRAWINGS

FIG. 1b is a block diagram illustrating a curvable or steerable stylet in isolation of the instrument into which it is inserted.

FIG. 2 is a simplified longitudinal cross section of the tip or distal portion of the instrument shown in FIG. 1a.

FIG. 5 is a simplified longitudinal cross sectional view of the distal portion of a instrument usable in the system of FIG. 4.

FIG. 6 is a perpendicular cross sectional view of the tip shown in FIG. 5 as seen through section line 6—6 of FIG. 5.

FIG. 7 is a simplified longitudinal cross sectional view of the distal tip of another embodiment of a instrument wherein a differential pull wire is utilized to impart a curvature to the tip.

FIG. 8a is perpendicular cross sectional view of the distal tip shown in the FIG. 7 as s seen through section lines 8—8 of FIG. 7.

FIG. 8b is perpendicular cross sectional view of the distal tip similar to that shown in the FIG. 7 as seen through section lines 8—8 of FIG. 7, wherein the cross section of the stylet has been modified to comprise a rectangular wire disposed in a U-shaped wire.

FIG. 9 is a longitudinal cross-sectional view of another implementation of the pull wire technique equivalent to what is generally described in connection with the system of FIG. 1.

FIG. 10 is a perpendicular cross sectional view of the distal tip of FIG. 9 as seen through section lines 10—10 of FIG. 9.

FIG. 11 is a simplified longitudinal cross sectional view of the distal portion of a instrument according to the invention.

FIG. 12 is a simplified longitudinal cross sectional view of the distal portion of another instrument according to the invention.

These and other embodiments or implementations of the invention may be better understood by now turning to the following detailed description.

DETAILED DESCRIPTION OF THE PREFERRED EMBODIMENTS

The invention comprises a means by which the distal tip of a cardiac instrument may be variably curved according to the physician control during implantation or other active use of the instrument. Whereas in the illustrated embodiment, the invention will be described in terms of a pacemaker instrument, it must be understood that any type of cardiac lead, now known or later devised, is contemplated as being expressly within the scope of the invention. For example, in addition to pacemaker leads, the invention is intended to specifically include cardiac defibrillation leads, ablation leads, and mapping or electrophysiological sensing leads, pulmonary artery catheters, central venous catheters, diagnostic coronary catheters, intra-aortic balloon pump catheters, balloon tipped (PTCA)/angioplasty catheters, and cardiac stent delivery catheters.

Figure 1A:
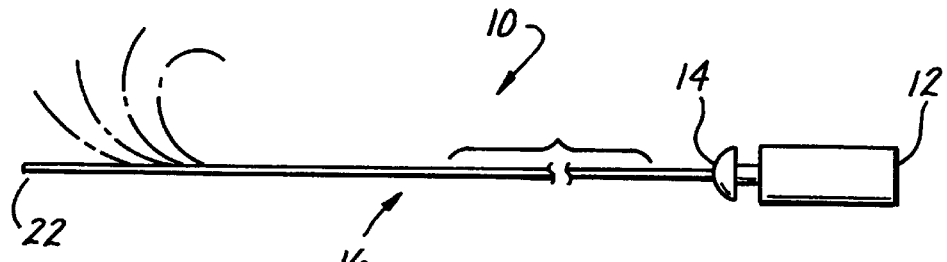
FIG. 1a is a block diagram illustrating the first embodiment of the invention in which a segmented terminal pin is utilized to manipulate a pull wire for providing a tip curvature of the instrument.
Figure 2:
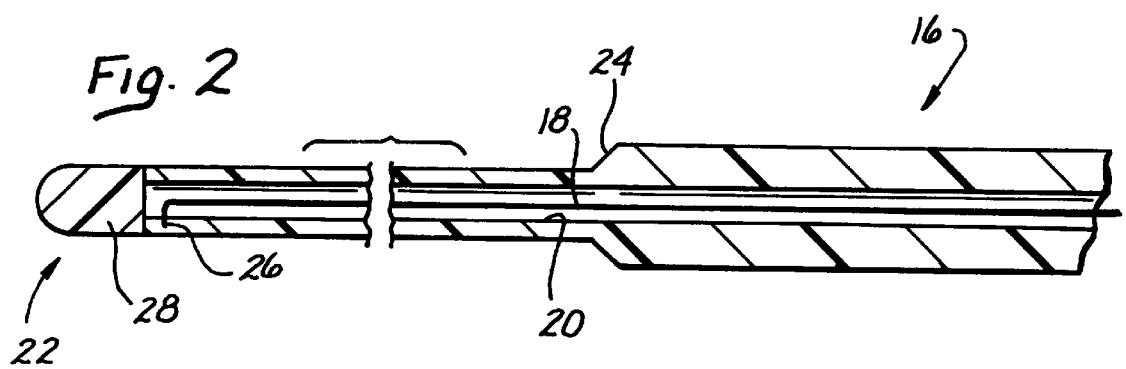
Figure 3:
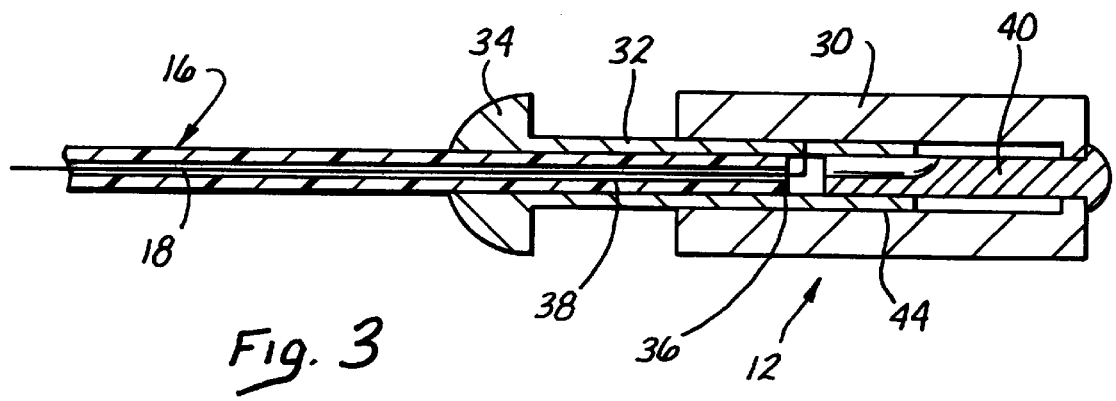
FIG. 3 is a simplified longitudinal cross section showing the proximal portion of the instrument in FIG. 1a, and in particular, the connection of the pull wire to the terminal pin.

The distal tip of the cardiac instrument may be variably and controllably curved by integrating a steering mechanism into the instrument construction itself as is in the case of the embodiment of FIGS. 1a, 2 and 3 or in a stylet which is inserted into a lumen within the instrument as is in the case with the embodiments of FIGS. 1b, 4–8, and 11–14 and the example of FIGS. 9 and 10. Therefore, it must be expressly understood that while only certain mechanisms for providing controllable curves in the distal tip are illustrated in the specification, any mechanism capable of providing the controlled curvature, including those beyond those specifically illustrated, is contained within the scope of the invention.

Turn first to the embodiment of FIG. 1a wherein the lead system, generally denoted by reference numeral 10, is diagrammatically depicted as being comprised of a segmented terminal pin 12 connected at the proximal end 14 of instrument 16. Terminal pin 12 is attached, for example, to a pull wire 18 best depicted in FIGS. 2 and 3, which is disposed in a longitudinally defined lumen 20 along the length of instrument 16 extending from its distal tip 22 to its proximal end 14. By drawing in or providing a tension on pull wire 18 as will be described in greater detail in connection with FIGS. 2 and 3, distal tip 22 of instrument 16 is drawn up or curved backwardly toward proximal end 14 as shown in dotted outline in FIG. 1a. Otherwise, the normal or relaxed configuration of instrument 16 is undeflected or straight as shown in solid outline in FIG. 1a. At the proximal end of the instrument is a terminal pin, a segment of which manipulates the distal tips flexion and the instruments overall column strength. When the terminal pin segment is rotated clockwise, for example, the instrument tip assumes a J-shaped contour, suitable for passage through the tricuspid valve, into the pulmonary outflow track, and into the right ventricle or atrial appendage. When the terminal pin is rotated counterclockwise, the instrument body becomes rigid, suitable for wedging the instrument or to perform instrument retraction in the event that it is required. Bringing the terminal pin to a center or neutral position, turns the tip to a straight nonrigid state.

FIG. 1b is a simplified abstract diagram illustrating a curvable or steerable stylet which may be used in the instrument of FIG. 1a. Stylet 17 is coupled at its proximal end 19 to a manipulatable handle 21, which by the various means discussed below includes a pushable, turnable, or selectively activatable element 23 which when selected causes at least the tip or other portion of stylet 17 to curve if straight or to straighten if curved.

In alternative embodiments, a J-curve may be prebiased within instrument 16 and advancement of wire 18 within its corresponding lumen 20 used to straighten distal tip 22. In this case pull wire 18 is actually more accurately referred to as a push wire. In the following the context of the description will make it clear whether a tension or compression is being applied to wire 18. In general the wire may be either pushed or pulled as needed. The instrument is supplied with a prebiased curve and when the terminal pin is rotated, the instrument becomes straight. Continuous deflections are possible between the straight and maximum curved position according to the user selection.

Consider the pull wire 18 in the embodiment of FIGS. 2 and 3. Distal tip 22 or instrument 16 is typically highly flexible and has a thinned diameter as compared to the more proximal portions of instrument 16 as provided by the narrowing of shoulders 24 shown in FIG. 2. Pull wire 18 is mechanically or adhesively fixed at point 26 near distal tip 22, such as immediately behind tip electrode 28. Tension applied on pull wire 18, drawing wire 18 back within its lumen 20, will therefore cause tip 22 to curve back toward the proximal end 14 as shown in FIG. 1a by varying degrees depending on the amount of tension and retraction applied to wire 18.

One means for providing the retractile force on wire 18 is shown in detail in terminal pin 12 of FIG. 3 which depicts a simplified longitudinal cross section of terminal pin 12. Terminal pin 12 is comprised of a body 30 which provides the primary hand-hold for the surgeon. A retractable piston 32, having a distal knob 44 to facilitate in its longitudinal displacement within cylindrical body 30, slip fits or is otherwise longitudinally displaceable within body 30. While piston 32 is easily movable within body 30 under manual pressure, the degree of friction or engagement between piston 32 and body 30 is such that the reactive tension of wire 18 created by the curvature of distal tip 22 is nevertheless insufficient to move piston 32 relative to body 30 once the physician has made an adjustment between them.

For example, wire 18 extends within instrument 16 and exits its proximal end 36 to be fixed, adhered or otherwise connected to piston 32. Likewise, instrument 16 is itself loosely disposed with an axial longitudinal bore 38 defined through piston 32 so that there is little, if any, frictional engagement between piston 32 and the outside surface of instrument 16. Meanwhile, a stop rod 40 having an axial longitudinal slot is connected to body 30, such as being screwed through its end wall 42, which stop rod extends into the longitudinal bore 38 of piston 32 to provide an abutting interference stop to proximal end 36 of instrument 16. However, longitudinal slot defined in rod 40 allows wire 18 to be disposed through the slot as piston 32 is pushed to the left in FIG. 3 thereby drawing wire 18 out of instrument 16.

It is to be expressly understood that terminal pin 12 is shown in only one embodiment and that many other types of structures may be employed for pulling or pushing wire 18 within its longitudinal lumen 20 of instrument 16. For example, instead of the telescopically slidable piston assembly of FIG. 3, piston 32 could be provided with external threading for threadable coupling to bore 44 of body 30. In this instance, a swivel connection through a washer or the like could be provided for the coupling between wire 18 and rotatable threaded piston 32 so that wire 18 is advanced or retracted by screwing piston 32 in or out of body 30.

Figure 4:
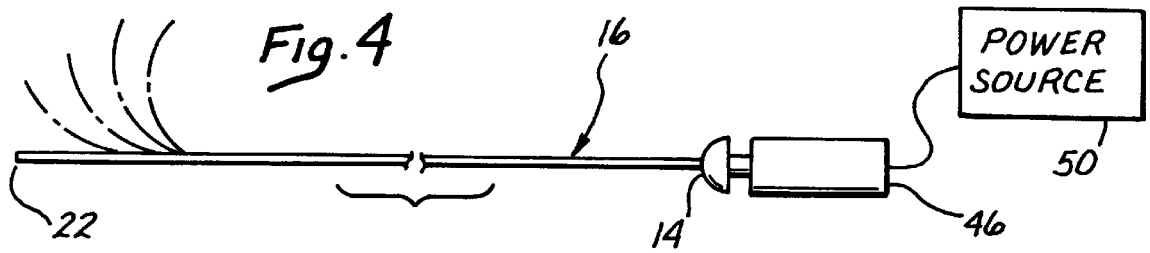
FIG. 4 is a simplified block diagram showing a second embodiment of the invention in which a stylet is utilized in the instrument and is thermoelectrically curved to control tip curvature of the instrument.

Another embodiment of the invention is depicted in FIG. 4 wherein a thermoelectrically curvable stylet as describe in connection with FIGS. 5 and 6 is utilized to impart the distal tip curvature to instrument 16. In the embodiment of FIG. 4, terminal pin 12 is replaced by a handle and electrical connector 46, which is connected to the proximal end of stylet 48 disposed within lumen 20 of instrument 16. Handle and connector 46 are then electrically coupled to a power source 50 which provides an appropriate voltage and current for heating the differential elements of stylet 48 to achieve the acquired curvature for the predetermined time.

Turning specifically to FIGS. 5 and 6, stylet 48 is shown as being comprised at least on part of its distal portion of a first strip 52 disposed adjacent to a second strip 54. Strips 52 and 54 are preferably made of different metals and electrically insulated from each other along their length except for distal portion 56 where they are electrically and physically coupled together. Current flows through one strip 52 through their electrical coupling at distal portion 56 and thence back to power source 50 through strip 54. Ohmic heating occurring in strips 52 and 54 cause the two materials to expand or contract at different rates, thereby creating an asymmetric tension along their length which in turn causes stylet 48 to curve if originally in the straight unbiased configuration or to uncoil if in an originally curved configuration and if the more thermally expansive strip 52 or 54 disposed on the inside of the curve much like a conventional bimetallic strip.

For example, a stylet of approximate 0.014 to 0.018 inch in outer diameter and in lengths varying from 40 to 60 centimeters is provided in which the proximal end of the stylet has a manipulation handle attached to a power source which is battery operated or line powered. The stylet is made of Nitenol, either alone or in combination with other materials. When the power source is activated, the tip of the stylet is deflected and assumes a curved contour suitable for manipulation through the tricuspid valve and into the pulmonary outflow track. When the power source if switched off, the tip returns to a straight configuration.

In another embodiment, the instrument is supplied in a prebiased curve form and when the power source is applied, it straightens. The degree of deflection between straight and the most curved position is continuous so that the degree of curvature is arbitrarily selected by the user.

It also must be understood that stylet 48 need not include the bithermal or bimetallic strip pair 52 and 54 along its entire length. Instead, the bimetallic portion may only be in the proximity of distal tip 22 with the remaining portion being a single wire. The two portions would then be in electrical contact with each other and the circuit completed by return wire connected at the distal end of the bimetallic strip and returning to current source 50.

The perpendicular cross section of stylet 48 is depicted in FIG. 6 as seen through section line 6—6 of distal tip 22. In the illustrated embodiment, strip portions 52 and 54 are shown as substantially in the form of half cylinders joined on their common diameter, either by an insulating layer 58, or conductive solder or other conductive layer in place of layer 58 depending upon whether strips 52 and 54 are utilized in the same portion of the circuitry in parallel or are serially connected as described above.

Furthermore, in both the embodiments of FIGS. 1–3 and 4–6, pull wire 18 or stylet 48 has been shown as being disposed in a central or axial lumen 20 of instrument 16. This need not be the case and other lumen cross sectional shapes and positions may be equivalently employed. For example, as will be described below in connection with the embodiment of FIGS. 8a and 8b, the lumen may have a noncircular perpendicular cross section to provide for angular fixation of pull wire 18 or stylet 48 within instrument 16 or may be positioned in an off axis lumen 60 defined within the wall thickness of instrument 16. Typically, multiple lumens are defined through the longitudinal length of instrument 16 for providing one or more electrical circuits to electrodes included on the instrument, such as tip electrode 28, or other sensing, ablation or defibrillation electrodes, which may be placed along its length.

Consider another example of the invention as shown in FIGS. 7 and 8a in which stylet 48 of the embodiment of FIGS. 5 and 6 are replaced by a stylet 62 disposed within a rectangular or square lumen 64 defined within instrument 16. Stylet 62 in this case is comprised of two pull wires 66 and 68. Pull wires 66 and 68 are shown in the perpendicular cross section of FIG. 8a as seen through section lines 8—8 of FIG. 7 as being rectangular in cross section and therefore comprise two longitudinal strips sandwiched together. Flat wire 66 and 68 may be fixed together at their distal end by soldering, crimping, adhering or any other means as symbolically denoted by coupling 70, which extends along the distal tip of stylet 62 for a predetermined distance 72. When one wire 66 or 68 is pushed or retracted with respect to the other by an appropriate handle mechanism at proximal end 14 of instrument 16, the resulting differential tension will cause the distal tip of stylet 62 to curve. The polygonal cross section of lumen 64 and the conforming cross section of stylet 62 prevents twisting of stylet 62, although cylindrical cross sections could be employed in applications where twisting is not a consideration or does not occur. A predefined degree of clearance between lumen 64 and the exterior envelope of stylet 62 permits the slight bowing of one wire 66 with respect to the other 68 or vise versa, to allow for the curving of stylet 62.

FIG. 8b is a perpendicular cross-sectional view of the stylet of FIG. 7 wherein the perpendicular cross-sectional shape of wires 66 and 68 have been modified from flattened rectangular shapes to a U-shape extrusion for wire 68' and a rectangular solid wire 66' which is disposed in and slides in the channel defined in U-shaped wire 68'.

Alternatively, while the above illustrated embodiment has been implicitly described in terms of nonextensible wires 66 and 68, it is also within the scope of the invention that wires 66 and 68 may be elastomeric, that is either stretchable or compressible. In this case, like the bimetallic coupling described in connection with FIGS. 5 and 6, one wire will compressed or stretched compared to the other, causing a differential tension across their interface, and hence, the curvature of stylet 62.

Therefore, it should be clear that any mechanism which can impress a curve into a stylet inserted into an elongated instrument, be it a lead or catheter, falls within the scope of the invention. Another example by which the invention may be implemented is shown in FIGS. 9 and 10. Again, FIG. 9 is a simplified longitudinal cross sectional view of distal portion 22 of instrument 16. In this example, stylet 72 is disposed within lumen 20 of instrument 16 as before, but is comprised of a resilient or flexible metal tube or cylinder 74, such as a helical spring in which a pull wire 76 has been coaxially disposed. Cylinder 24 is a hollow spring, typically of 0.014–0.018 inch in diameter. Pull wire 76 is a solid thinner wire coaxially disposed within a lumen 28 defined within cylinder 74 and fixed at or near distal end 80 of stylet 72. Tension applied to pull wire 76 will thus cause at least distal portion 28 to curve substantially in the same manner as described above in connection with the embodiments of FIGS. 1–8.

In another embodiment, such as shown in FIG. 11, instrument 16 is provided with a portion 82 in which the wall 84 of instrument 16 is defined with an accordion or wrinkled skin. The degree of wrinkling is molded in and extends around the cross section of instrument 16 by predetermined amount, such as approximately halfway around the circumference, so that the opposing portion 86 of wall 84 of instrument 16 is substantially smooth or unwrinkled. Air or fluid pressure then injected, or even simply a push wire inserted, into lumen 88 will cause portion 82 to unfold while the opposing portion 86 remains taut and comparatively nonextendable. This will cause a distal portion of instrument 16 to curve away from wrinkled portion 82. Removal of the pressure allows instrument 16 to resume its nonextended configuration, namely it allows the accordion folds or wrinkles in portion 82 to return to their original configuration due to the resiliency of the material of which instrument 16 is made, thereby straightening the distal portion of instrument 16. Straightening is urged both by the compression of material comprising smooth portion 86 as well as the tension of resilient material comprising portion 82.

The differential expandability of opposing wall portions of instrument 16 may be achieved by other equivalent means such as depicted diagrammatically in FIG. 12 wherein an entire cylindrical segment of wall 84 of instrument 16 has been shaped in the form of an accordion, like a flexible straw or hose. However, one side of the accordion envelope 90 has been interiorly filled with a comparatively nonextensible adhesive 92 to achieve a differential tension when lumen 88 is inflated by pressurized fluid.

The embodiments of FIGS. 11 and 12 have the advantage that lumen 88 can be pressurized to a first level which renders a highly flexible instrument rigid, but without substantially expanding the pleated or accordion section of the distal portion. As the pressure increases to a second higher level, the pleated or accordion portion 82 or 90 is then unfolded with resulting curvature.

Figure 13:
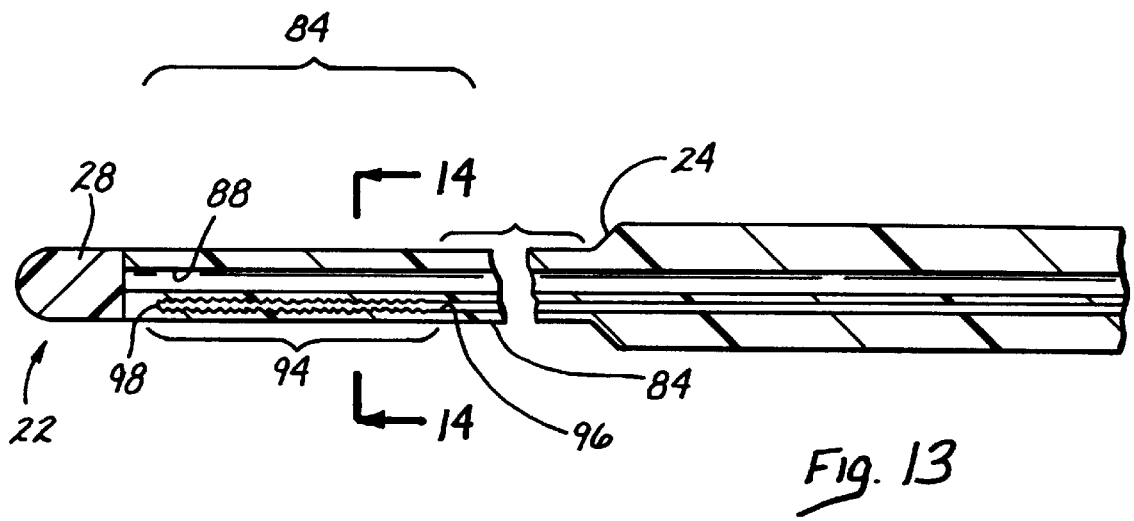
FIG. 13 is a simplified longitudinal cross sectional view of the distal portion of yet another instrument according to the invention.
Figure 14:
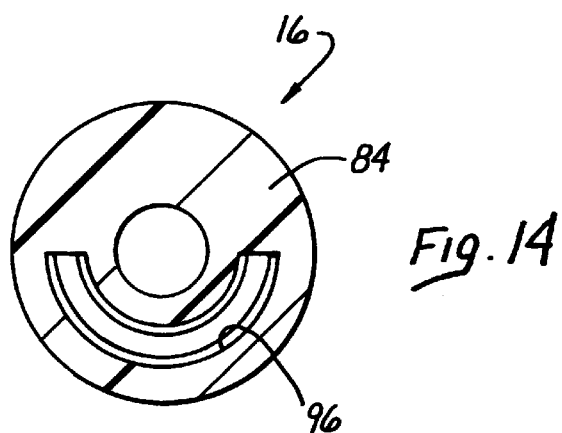
FIG. 14 is a perpendicular cross sectional view of the distal tip of FIG. 13 as seen through section lines 14—14 of FIG. 13.

Opposing wall 84 in portion 86 may be thinned at a predetermined section 94 to assist in the ease of bending and definition of the curvature of the distal portion of instrument 16. In fact, the pleated or accordion portion 82 or 90 may be greatly exaggerated in the form of a bellows to achieve acute bends and define points of bend along the length of instrument 16. In the case where pleating or wrinkling of the exterior surface of instrument 16 cannot be tolerated, the wrinkling or pleating may be entirely formed interiorly within lumen 88 and the exterior of instrument 16 provided at that section with a smooth highly extensible thin skin. For example, as shown in FIG. 13, distal portion 94 of instrument 16 is provided with an off-axis lateral lumen 96 defined within wall 84 along distal portion 94. The interior surface of lumen 96 in distal portion 94 is wrinkled or pleated so that when pressurized by fluid, the extensible material of which wall 84 is comprised, tends to extend longitudinally along the axis of lumen 96 in opposition to the comparatively nonextendable portion of the opposite side of wall 84 thereby resulting in a curvature of the distal tip.

Alternatively, instead of pressurizing lumen 96, a push wire or stylet (not depicted) may be disposed within in lumen 96 to push against end 98 of lumen 96 thereby extending or stretching the pleated distal portion 94 relative to the opposing wall portion 96, again resulting in the same differential tension and curvature of the instrument tip. In the case where a single lumen 96 and push wire is insufficient to provide enough differential tension across the cross section of instrument 16, a plurality of such lumens may be employed in parallel all on one half circle of the instrument cross section. Similarly, instead of a push wire, a pull wire may be employed so that lumen 96 compressed along its pleated section in the situation where the pull wire is attached to end 98 such as to a small compression plate which may be embedded in wall 84. In the foregoing, lumen 96 need not be assumed to be circular in cross section, but may be free form in its cross-sectional shape assuming instead the arcuate cross section depicted in FIG. 1a4 to thereby accommodate substantially greater extendibility or compressibility of the pleated section. Similarly, the push wire or pull wire disposed therein may have a similarly conforming or space-filling shape to act in the manner of a stylet internal to wall 84 and thereby to be more conveniently handled as a single piece rather than as a plurality of small circular wires.

Figure 15:
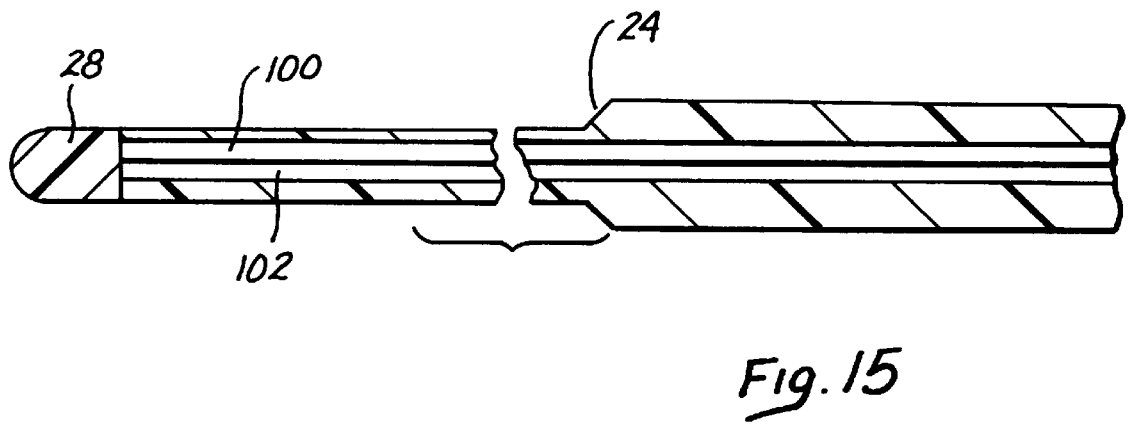
FIG. 15 is a simplified longitudinal cross sectional view of the distal portion of still another instrument according to the invention.

FIG. 15 illustrates another embodiment in which the differential tension or compression used to curve or steer the elongated instrument is created by a pressurizable longitudinal lumen 100 defined in instrument 16 and an opposing tensile nonmetallic filament 102 embedded into instrument 16 or disposed in another lumen. For example, filament 102 may be a Dacron or substantial nonstretchable filament disposed off-center in a lumen and attached at its distal end to tip 28 or an adjacent tip portion. Tension applied to filament 102 will therefore cause the tip of instrument 16 to curve back on itself. In the case where instrument 16 is very flexible and does not have sufficient resiliency in its walls to restraighten itself after the tension is removed, as is the case with a pacemaker lead, lumen 100 is pressurized with saline causing instrument 16 to temporarily assume a rigid straight configuration. After the fluid pressure is removed, instrument 16 then reassumes its limp, flexible and undefined shape. In one embodiment filament 102 may in fact be disposed in lumen 100, which is then is defined in instrument 16 in an off or on axis position as may be desired.

Alternatively, lumen 100 can be made telescopic by an accordion construction or inherent resiliency or both, and filament 102 disposed therein to apply a tensile force to compress or bend lumen 100 back on itself Filament 102 could also be disposed in a parallel offset lumen of its own and brought around a direction changing pulley-like distal bend (not shown) and attached to the distal end of lumen 100 to apply a stretching force on lumen 100, which would tend to straighten it or even to pull itself over on itself in a bend. In such an embodiment the inflation of lumen 100 would become unnecessary, since it would be established by tension on filament 102. Pairs of such filaments 102 could then be employed, one filament disposed in or near lumen 100 and arranged to compress lumen 100 by a tensile force from that filament, and the other filament disposed in an opposing parallel lumen and arranged to stretch lumen 100 by a tensile force from that other filament. The tip of the instrument could then be pulled back on itself to form a curve or straightened out by pulling on either one of the two filaments to control the tip like a marionette.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An improvement in a flexible pacemaker or defibrillator lead having a proximal and distal portion, and a longitudinal lumen defined at least part way therein, said pacemaker or defibrillator lead being without prebiased shape for permanent compatibility in a heart, comprising:

a stylet disposed in said lumen within at least said distal portion, said stylet provided to selectively define a curvature on said distal portion of said pacemaker or defibrillator lead according to user determination, wherein said stylet comprises a filament disposed within said lumen and attached at a distal end of said filament at said distal portion of said pacemaker or defibrillator lead, a proximal end of said filament extending to said proximal portion of said pacemaker or defibrillator lead and being retractable at least to a degree from said lumen to cause said distal portion to curve by user-selected amounts, and further comprising an inflatable lumen defined within said pacemaker or defibrillator lead for straightening said pacemaker or defibrillator lead when said inflatable lumen is pressurized with a fluid, whereby variable curvatures can be selectively defined within said distal portion of said pacemaker or defibrillator lead.

2. The improvement of claim 1 wherein said lumen in which said filament is disposed comprises said inflatable lumen.

3. An improvement in an elongated, body invasive instrument having a proximal and distal end and a longitudinal lumen defined at least part way therein comprising:

a single piece deflectable stylet temporarily disposable in said lumen within at least said distal portion of said instrument and selectively removable therefrom while leaving said instrument in place, said deflectable stylet being deformable by user manipulation of said stylet from a proximal end of said stylet to selectively impose a curvature on said distal portion of said instrument according to user determination, said instrument being free of any prebiased shape, wherein said deflectable stylet comprises a stylet body, and a pull wire disposed adjacent to said stylet body and attached at a distal end of said pull wire to a distal portion of said stylet body, a proximal end of said pull wire extending to a proximal portion of said stylet body and being retractable at least to a degree to cause said distal portion of said stylet body to curve by user-selected amounts, whereby variable curvatures can be selectively defined within said distal portion of said instrument.

4. An improvement in an elongated, body invasive instrument having a proximal and distal end and a longitudinal lumen defined at least part way therein comprising:

a single piece deflectable stylet temporarily disposable in said lumen within at least said distal portion of said instrument and selectively removable therefrom while leaving said instrument in place, said deflectable stylet being deformable by user manipulation of said stylet from a proximal end of said stylet to selectively impose a curvature on said distal portion of said instrument according to user determination, said instrument being free of any prebiased shape, wherein said stylet is comprised at least in part of a pair of differentially slidable wires connected at one end to each other and disposed within said distal portion of said instrument, differential tension of said wires with respect to each other causing said pair of wires to curve and hence said distal portion of said instrument therewith, wherein said pair of differentially slidable wires comprise a flexible outer resilient cylinder and an inner pull wire disposed within said cylinder, whereby variable curvatures can be selectively defined within said distal portion of said instrument.

5. An improvement in a method for variably controlling the shape of an instrument while being manipulated in a body comprising:

curving a stylet disposed within a longitudinal lumen within said instrument at least along a distal portion of said instrument; and conformably curving said distal portion of said instrument in response to curvature of said deflectable stylet, said deflectable stylet being curved according to user selection, where said stylet comprises a first and second longitudinal element and where curving said deflectable stylet comprises establishing a differential tension between a first and second longitudinal element in at least said distal portion of said stylet, the degree of said differential tension determining the degree of curvature of said distal portion, wherein establishing said differential tension comprises withdrawing a pull wire disposed in said longitudinal lumen defined in said instrument wherein said pull wire is fixed at its distal end to said distal portion of said instrument, said first longitudinal element comprising a body of said stylet and said second longitudinal element comprising said pull wire.

6. An improvement in a method for variably controlling the shape of an elongated invasive instrument comprising:

curving at least a distal portion of said instrument by differentially expanding or compressing one side portion of said instrument with respect to an opposing side portion of said instrument by operation of a telescoping portion of said one side portion of said instrument, where curving at least a distal portion of said instrument by differentially expanding or compressing one side portion of said instrument with respect to an opposing side porion of said instrument comprises applying a tensile force through a filament to a folding lumen defined in said one side portion of said instrument.

7. An improvement in an elongated, body invasive instrument having a proximal and distal end and a longitudinal lumen defined at least part way therein comprising:

a single piece deflectable stylet temporarily disposable in said lumen within at least said distal portion of said instrument and selectively removable therefrom while leaving said instrument in place, said deflectable stylet being deformable by user manipulation of said stylet from a proximal end of said stylet to selectively impose a curvature on said distal portion of said instrument according to user determination, said instrument being free of any prebiased shape, wherein said stylet is comprised at least in part of a pair of differentially slidable wires connected at one end to each other and disposed within said distal portion of said instrument, differential tension of said wires with respect to each other causing said pair of wires to curve and hence said distal portion of said instrument therewith, wherein said pair of differentially slidable wires comprise a flexible outer resilient cylinder and an inner pull wire disposed within said cylinder, and wherein said inner pull wire is coaxial within said cylinder in at least a distal portion thereof, whereby variable curvatures can be selectively defined within said distal portion of said instrument.

8. An improvement in an elongated, body invasive instrument having a proximal and distal end and a longitudinal lumen defined at least part way therein comprising:

a single piece deflectable stylet temporarily disposable in said lumen within at least said distal portion of said instrument and selectively removable therefrom while leaving said instrument in place, said deflectable stylet being deformable by user manipulation of said stylet from a proximal end of said stylet to selectively impose a curvature on said distal portion of said instrument according to user determination, said instrument being free of any prebiased shape, wherein said stylet is comprised at least in part of a pair of differentially slidable wires connected at one end to each other and disposed within said distal portion of said instrument, differential tension of said wires with respect to each other causing said pair of wires to curve and hence said distal portion of said instrument therewith, wherein said pair of differentially slidable wires comprise a flexible outer resilient cylinder and an inner pull wire disposed within said cylinder, and wherein said inner pull wire is eccentric within said cylinder in at least a distal portion thereof, whereby variable curvatures can be selectively defined within said distal portion of said instrument.

* * * * *